United States Patent
Hsu et al.

(10) Patent No.: US 8,301,257 B2
(45) Date of Patent: Oct. 30, 2012

(54) METHOD FOR SUPPRESSING AND REVERSING EPILEPTOGENESIS

(75) Inventors: David Ambrose Hsu, Middleton, WI (US); Murielle Aline Hsu, Middleton, WI (US); John Matthew Beggs, Bloomington, IN (US)

(73) Assignee: Wisconsin Alumni Research Foundation, Madison, WI (US)

( * ) Notice: Subject to any disclaimer, the term of this patent is extended or adjusted under 35 U.S.C. 154(b) by 477 days.

(21) Appl. No.: 12/426,430

(22) Filed: Apr. 20, 2009

(65) Prior Publication Data

US 2009/0264958 A1    Oct. 22, 2009

Related U.S. Application Data

(60) Provisional application No. 61/046,465, filed on Apr. 21, 2008.

(51) Int. Cl.
*A61N 1/00* (2006.01)
(52) U.S. Cl. .......... 607/45; 600/373; 600/378; 600/544; 600/545; 606/130; 607/1; 607/2; 607/46; 607/59; 607/115; 607/116
(58) Field of Classification Search .................. 600/373, 600/378, 544, 545; 606/130; 607/1, 2, 45, 607/46, 59, 115, 116
See application file for complete search history.

(56) References Cited

U.S. PATENT DOCUMENTS

| 6,549,804 B1 * | 4/2003 | Osorio et al. | 600/544 |
| 2007/0027486 A1 * | 2/2007 | Armstrong | 607/2 |

OTHER PUBLICATIONS

Wierenga et al, Postsynaptic expression of homeostatic plasticity at neocortical synapses. J Neurosci, 2005. 25 (11): p. 2895-905.
Beggs et al, Neuronal avalanches in neocortical circuits. J Neurosci, 2003. 23(35): p. 11167-77.
Beggs et al, Neuronal avalanches are diverse and precise activity patterns that are stable for many hours in cortical slice cultures. J Neurosci, 2004. 24(22): p. 5216-29.
Chialvo D.R., Critical brain networks. Physica A: Statistical Mechanics and its Applications, 2004. 340(4): p. 756-765.
Chialvo D.R., Psychophysics: Are our senses critical? Nat. Phys., 2006. 2: p. 301-302.
Destexhe et al, Plasticity in single neuron and circuit computations. Nature, 2004. 431(7010): p. 789-95.
Eguiluz et al., Scale-free brain functional networks. Phys Rev Lett, 2005. 94(1): p. 018102.
Lemasson et al, Activity-dependent regulation of conductances in model neurons. Science, 1993. 259(5103): p. 1915-7.
Madhavan et al, Plasticity of recurring spatiotemporal activity patterns in cortical networks. Phys. Biol., 2007. 4: p. 181-193.
Plenz et al, The organizing principles of neuronal avalanches: cell assemblies in the cortex? Trends Neurosci, 2007. 30(3): p. 101-10.

(Continued)

*Primary Examiner* — Niketa Patel
*Assistant Examiner* — Lindsey G. Hankins
(74) *Attorney, Agent, or Firm* — Quarles & Brady, LLP; Jonathan D. Stone

(57) ABSTRACT

A method for identifying, suppressing, and reversing epileptogenesis, which is considered to be a learned response due to brain plasticity. The method includes identifying three epileptogenic conditions, neuronal hyperexcitability, spatial overconnectivity, and temporal overconnectivity. A treatment that accounts for each of these conditions is then be administered to the subject to reverse, or "unlearn," epilepsy.

11 Claims, 3 Drawing Sheets

OTHER PUBLICATIONS

Rolston et al, Precisely timed spatiotemporal patterns of neural activity in dissociated cortical cultures. Neuroscience, 2007. 148: p. 294-303.

Stewart et al, Inverted-U profile of dopamine-NMDA-mediated spontaneous avalanche recurrence in superficial layers of rat prefrontal cortex. J Neurosci, 2006. 26(31): p. 8148-59.

Stewart et al, Homeostasis of neuronal avalanches during postnatal cortex development in vitro. J Neurosci Methods, 2007.

Turrigiano et al, Activity-dependent changes in the intrinsic properties of cultured neurons. Science, 1994. 264 (5161): p. 974-7.

Turrigiano, G.G., Homeostatic plasticity in neuronal networks: the more things change, the more they stay the same. Trends Neurosci, 1999. 22(5): p. 221-7.

Turrigiano et al, Hebb and homeostasis in neuronal plasticity. Curr Opin Neurobiol, 2000. 10(3): p. 358-64.

* cited by examiner

SIMPLE CHAIN DIAGRAM WITH ONE INTERMEDIATE NODE

SIMPLE BRANCHING DIAGRAM WITH TWO PARALLEL INTERMEDIATE NODES

METHOD FOR SUPPRESSING AND REVERSING EPILEPTOGENESIS

CROSS REFERENCE TO RELATED APPLICATION

This application is based on, claims the benefit of, and incorporates herein by reference U.S. Provisional Application Ser. No. 61/046,465, filed Apr. 21, 2008, entitled "METHOD FOR SUPPRESSING AND REVERSING EPILEPTOGENESIS."

STATEMENT REGARDING FEDERALLY SPONSORED RESEARCH

This invention was made with United States government support awarded by the following agency: NIH RR025012. The United States government has certain rights in this invention.

BACKGROUND OF THE INVENTION

The field of the invention is methods and devices for detecting and suppressing epileptogenic states and/or reversing such epileptic circuits once formed.

The primary functions of the brain are to transmit, process, and store information about the body and the environment. Higher order functions such as problem solving and adaptation also exist in some animals and these functions may be loosely referred to as components of the learning process. The plasticity of neurons and connections between neurons is central to these capabilities. However, plasticity is also central to epileptogenesis and prior art methods for identifying or treating epilepsy cannot explain why plasticity plays a role in both learning and epileptogenesis. There are an enormous number of ways in which plasticity can go wrong at all levels of description, particularly at the genetic level, where the process of epileptogenesis is bewilderingly complex with many contributory factors. Indeed, so intricately is normal brain function dependent on the proper mix of receptors, channels, chemical environment, and other factors that it can be surprising that epilepsy is not more prevalent.

Current approaches for treating epilepsy using electrical stimulation, such as vagal nerve, cortical and deep brain stimulation, are empirical. It is unclear how these methods work and optimizing treatment generally involves trying different stimulation protocols and determining by observation over time which works better. Because people respond differently to any given protocol, it is typically not possible to design an optimal protocol for any single individual or condition other than by trial and error. In addition, current approaches target neuronal hyperexcitability caused by imbalances between excitatory and inhibitory influences at synapses, but do not consider other patterns of neural activity that may have a significant effect on epileptogenesis, for example, patterns occurring between large groups of neurons. It is believed that this limits the effectiveness of current methods for treating epileptogenesis.

It would therefore be desirable to have a method for identifying, suppressing, and reversing epilepsy that account for factors other than neuronal hyperexcitability, particularly those related to brain plasticity.

SUMMARY OF THE INVENTION

The present invention overcomes the aforementioned drawbacks by providing a method for identifying, suppressing, and reversing epilepsy. The method characterizes epilepsy as a "learned response" whose occurrence is dependent upon neuronal hyperexcitability and spatial and temporal overconnectivity in the brain. By modeling epilepsy in this way, the present invention provides a method for "unlearning" epilepsy.

The present invention provides a method for identifying and reducing a subject's risk of epilepsy. The method includes acquiring neural activity data from the subject and analyzing the acquired neural activity data by generating a parameter indicative of neuronal hyperexcitability due to imbalances between excitatory and inhibitory influences, and generating a parameter indicative of spatial overconnectivity that leads to abnormally wide spreads of neuronal activity, and generating a parameter indicative of temporal overconnectivity that leads to abnormally persistent neuronal activity. Then, epileptic patterns in the subject are determined based on the generated neuronal hyperexcitability, spatial connectivity, and temporal connectivity parameters and a treatment is administered to the subject to reverse the determined epileptic patterns.

Various other features of the present invention will be made apparent from the following detailed description and the drawings

GENERAL DESCRIPTION OF THE INVENTION

Figure 1:
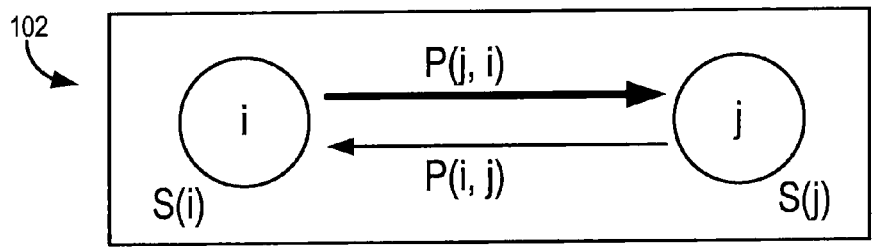
FIG. 1 is a schematic depiction of a nodal model of neural connectivity in accordance with the present invention.

As a consequence of the organizational principles for the functional behavior of biological neural systems, the ability of a neural system to learn appears to confer an intrinsic vulnerability to epileptogenesis. The present invention characterizes epilepsy as an abnormal "learned" response at the network level of such a system to repeated provocations and therefore provides a method for reversing, or "unlearning", epilepsy. Prior methods for treating epilepsy only addressed neuronal hyperexcitability due to an imbalance between excitatory and inhibitory influences. However, the present invention includes a method for reversing epilepsy that includes two other factors, overconnectivity in space leading to abnormally wide spreads of neuronal activity and overconnectivity in time leading to abnormally persistent activity.

Neural systems may be considered to obey Hebbian learning rules, which are best summarized by the phrase "cells that fire together, wire together." In the simplest formulation, if two neurons consistently fire consecutively, then the connection from the first-firing neuron to the second-firing neuron is strengthened. This learning rule represents long-term potentiation (LTP). Conversely, if the firing of a first neuron is not followed by the firing of a second neuron, then the connection of the connection between the two neurons is weakened. This learning rule represents long-term depression (LTD). A third learning rule known as the spike-timing dependent plasticity (STDP) combines both LTP and LTD. Generally, these learning rules are referred to as competitive associative rules.

Computer simulations utilizing Hebbian learning rules tend to result in either runaway excitation or global silence. At the same time, spatial connectivity tends to steer towards either an overconnected state in which excitation at a neuron is immediately followed by global or near-global activation or an underconnected state in which excitation at a neuron is not followed by the activation of any other neuron. Neither of these connectivity extremes is useful for information processing and the most useful connectivity levels lie somewhere in between to allow for a wide variety of spatial activation patterns from the smallest possible clusters of simultaneously discharging neurons to the largest possible areas covering macroscopic portions of the brain.

It has been shown that cortical slice networks produce cascades of activity such that the distribution of sizes follows a power law. This behavior may be referred to as a "neuronal avalanche." Similar power law distributions of sequence sizes have been reported in awake behaving monkeys, the isolated leech ganglion, and in dissociated cultures of neurons. This suggests that neuronal avalanches are a general phenomenon, reflecting a fundamental property of neuronal networks. Additionally, the power law of avalanche sizes suggests that these neural networks are operating near a "critical point," so named because the power laws are reminiscent of the critical point of phase transitions of matter despite lacking the property of universality. A critical neural system is balanced between a phase in which activity is dampened and a phase in which activity is expanding. This balanced state can be characterized by a branching ratio $\sigma$, which gives the average number of "descendant" neurons activated by a single "ancestor" neuron in a previous time step. This is expressed as follows:

$$\sigma = \frac{\text{Descendants}}{\text{Ancestors}}. \quad \text{Eqn. 1}$$

Essentially the branching ratio expresses that if one neuron fires an action potential, it will on average cause $\sigma$ neurons to fire in response. Experiments have shown that the branching ratio tends to hover very near to $\sigma=1$ and simulations have shown that this branching ratio does in fact provide a power law size distribution. Thus, systems having $\sigma=1$ are referred to as "critical" systems, while systems having $\sigma<1$ and $\sigma>1$ are referred to as subcritical and supercritical systems, respectively. Computational modeling studies suggest that networks operating at the critical point can simultaneously optimize information processing and storage, computational power, and stability. When the network deviates from the critical point, information processing and stability are compromised. A neural network whose job it is to process information, learn, and adapt must therefore maintain criticality, even as synaptic weights change strength during the process of learning. This suggests why biological neural systems tend to maintain criticality, because, in the face of the destabilizing effects of learning, maintaining criticality re-stabilizes the system and allows the system to continue learning.

Referring to FIG. 1, the present invention characterizes supercritical systems where $\sigma>1$ as epileptogenic, thereby implying that spatial overconnectivity is an important factor in the occurrence of spontaneous seizures. The present invention may employ a simple, node-based model, such that indicated at 102 to analyze the effect of provocations, such as status epilepticus and acute deafferentation (such as occurs in post-traumatic brain injury) on criticality and inducing epileptic seizures. In this model, a local grouping of neurons is represented by a node that can fire a population spike either spontaneously with no input from other nodes or in response to activity at other nodes. According to the model, at a given time t, the probability that node i fires spontaneously within a selected time window is given by S(i;t), which can differ between nodes and can also vary in time. At any given time, the conditional probability that a prior population spike at node j causes a population spike at node i within a selected time window is given by P(i, j;t). This conditional probability can differ between each pair of nodes and can vary in time. Therefore, the branching ratio can be defined as the sum of outputs to all other nodes:

$$\sigma(i, t) = \left\{ \sum_{j=1}^{N} P(j, i; t) \right\}. \quad \text{Eqn. 2}$$

A corresponding measure of excitatory input at a given node i can be given by the input ratio, which is defined as:

$$\eta(i, t) = \left\{ \sum_{j=1}^{N} P(i, j; t) \right\}. \quad \text{Eqn. 3}$$

While the branching ratio is a pre-synaptic attribute and the input ratio is a post-synaptic attribute, they are both measures of connectivity. Critical connectivity occurs when the branching and input ratios are at unity. As will be described later, unlearning epilepsy can involve applying stimuli to "tune" the branching ratios to acceptable values and restore critical connectivity.

As mentioned above, prior art methods for reducing epilepsy risk only focus on reducing neuronal hyperexcitability. However, maintaining firing rate homeostasis alone will not guarantee that critical homeostasis is maintained. In the presence of Hebbian learning, critical and firing rate homeostasis are independent principles and both must exist for a neural system to be algorithmically stable. It has been noted from the model that the scaling of the P(i, j;t)'s must operate more quickly than the scaling of the S(i;t)'s and that the greater this relative difference in scaling speed, the more stable the system. Further, it is important to distinguish spontaneous-related activity from connectivity-related activity, that is, activity due to S(i;t) versus P(i, j;t), because the two types of activity often do not change in parallel. In fact, they often change to counterbalance each other.

For example, forced increased activity in a subset of neurons during a simulated seizure was found to trigger homeostatic mechanisms that scale down all S(i;t)'s and P(i, j;t)'s to very small values. When the simulated seizure stops, homeostasis causes the S(i;t)'s and P(i, j;t)'s to recover to baseline values. However, since the scaling of the P(i, j;t)'s operates more quickly than the scaling of the S(i;j)'s, the total connectivity as measured by either branching or input ratio can overshoot steady state values for a time until the spontaneous firing probabilities, the S(i;j)'s, return to steady state values. Therefore, in the post-ictal state, the overall activity is decreased relative to baseline, but the level of connectivity is supercritical. As a result, if a population spike occurs in the post-ictal period, there is an increased chance of an excitation having an abnormally wide spatial spread. If such a hyperextended state occurs frequently enough in a learning system, then it will be "learned" and "burned" into memory. If the state is burned into memory, then there is an increased likelihood that the state will be reactivated at some random time in the future. The reactivation of spatially hyperextended states is a necessary condition for epilepsy, as seizures in epilepsy tend to start from the same focus in a stereotypic way and each seizure focus must involve a macroscopic number of neurons to generate clinical symptomatology. Thus, it has been determined that prolonged post-ictal states are epileptogenic, while shorter seizures with no post-ictal state are not as epileptogenic.

When only the effects of neuronal hyperexcitability and spatial overconnectivity are considered by the model of the present invention, simulations of epilepsy showed an increased activation of spatially hyperextended states, but did not show the rhythmic, hyperactive, and repetitive activation of spatially hyperextended states that is expected in seizures. This is reflected in the well-known phenomenon of isolated interictal spikes seen on clinical scale EEG's that represent a state of local supercritical connectivity, spanning brain areas from millimeter to centimeter lengthscales. However, these activation patterns do not represent seizures because they do not persist and patients exhibit minimal to no clinical manifestations during their occurrence. It was therefore determined that overconnectivity in time is also an important factor in the occurrence of spontaneous seizures.

Typical models for neuronal activity are Markovian, that is, inputs from times earlier than one step back are "forgotten." Markovian connectivity is adequate for coding static memory, but is not reliable for coding temporal sequences because temporal links induced by Markovian connectivity are fragile. This can be seen by considering five distinct patterns of spatial activation, A, B, C, D, and E. A Markovian brain trying to learn the temporal sequence A→B→C→D→E would learn the sequence as four separate links, A→B, B→C, C→D, and D→E. The disruption of any one of the four links by chance would cause the loss of the whole sequence. For example, if pattern C misfires, there is no way to look back further in time and see that it was preceded by patterns B and A and that, therefore, the current pattern is probably C and the next pattern should be D.

Figure 2:
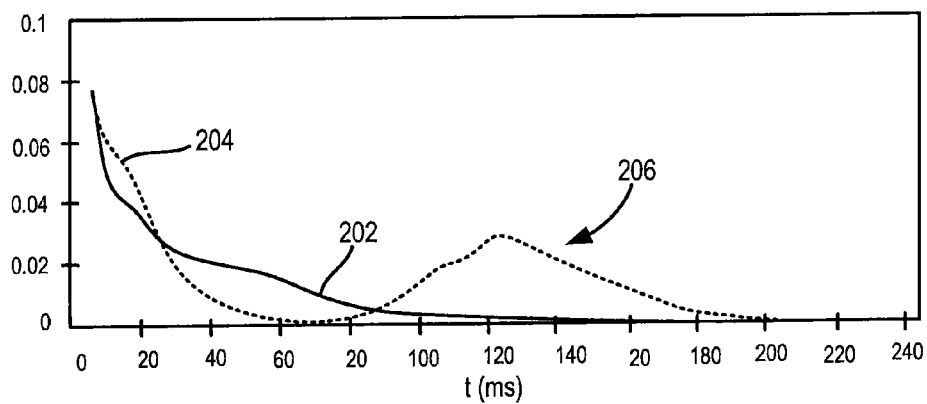
FIG. 2 shows cross-correlograms for Markovian and non-Markovian neural networks in accordance with the present invention.

The ability to look further back in time requires non-Markovian connectivity. In a non-Markovian brain where $P(i, j;t)$ is allowed to remember what happened four time steps back, the temporal sequence A→B→C→D→E can be learned in its entirety. If a given pattern misfires, it may be possible that the correct firing of previous patterns contains enough information to "skip over" the misfired pattern to finish the remainder of the sequence correctly. Relating this to epileptogenesis, if plastic non-Markovian connectivity exists in the brain, then it would be possible for a looping temporal sequence such as A→B→C→A→B→C→etc. to be created or accidentally learned. Non-Markovian connectivity can be detected using a cross-correlogram in the time domain, as shown in FIG. 2. A cross-correlogram 202 for a purely Markovian network typically decays quickly and monotonically (exponentially) in time, while a cross-correlogram 204 for a network with both Markovian and non-Markovian connectivity generally extends beyond the quick initial period of exponential decay and may have a long-time shoulder 206 or distinct bumps that occur at more substantial delays. It is contemplated that non-Markovian activity corresponds to the micro-oscillations that have been observed in epileptic brains. Temporal overconnectivity, when combined with the conditions of neuronal hyperexcitability and spatial overconnectivity, should result in an electrographic seizure.

Therefore, according to the present invention, the three conditions for epilepsy are neuronal hyperexcitability, spatial overconnectivity, and temporal overconnectivity. While these conditions need not be present continuously in an epileptic brain, it is contemplated that they must all exist for spontaneous seizures to occur. Therefore, to reduce a subject's risk of epilepsy, the present invention allows these conditions to be analyzed and characterized. Because prior art techniques exist for identifying and addressing neuronal hyperexcitability, only methods for treating spatial and temporal overconnectivity will be discussed in detail.

The degree of spatial overconnectivity in a subject can be assessed by determining a branching ratio for the subject. One technique for determining the branching ratio includes employing an adapted version of the Ornstein-Zernike equation, which is typically used in condensed matter physics to combine microscopic intermolecular interactions in various ways and estimate a direct correlation from which the total correlation function can be calculated. The present invention reverses this process by measuring the total correlation function experimentally and employing the Ornstein-Zernike equation to estimate the direct correlation function therefrom. This estimate is valid for Markovian and non-Markovian connectivity and for low and moderately elevated values of the branching ratio.

Figure 3:
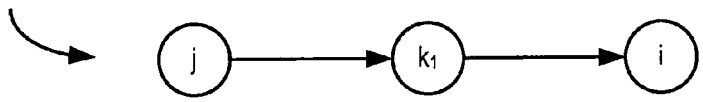
FIG. 3 depicts different branching patterns between nodes in accordance with the present invention.
Figure 3:
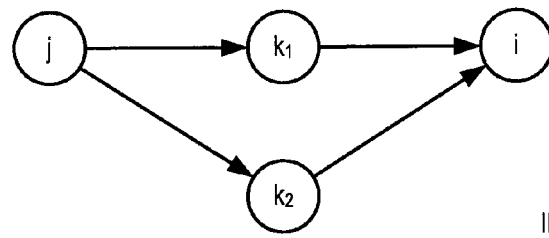

Pairwise cross-correlograms can be used to identify a casual relationship between unit potentials or populations spikes occurring at two different electrodes, but cannot be used to directly calculate a branching ratio, because, in addition to the direct correlation, pairwise cross-correlograms also implicitly include cross-correlations between many intermediate interactions. That is, the cross-correlogram $C(i, j;t)$ contains not just the interaction j→i (by which it is meant that a population spike at node j directly causes a spike at node i), but it also contains interactions from "chain diagrams" such as j→$k_1$→i, j→$k_1$→$k_2$→i, and all other higher order chain diagrams as well as all possible "branching" diagrams such as those shown in FIG. 3. The adapted Ornstein-Zernike equation is employed to extract an approximation of the direct-correlation from the total correlogram. If $D_{OZ}(i,j;t)$ is the Ornstein-Zernike estimate of the direct correlation function, then it can be related to the total correlogram by:

$$C(i, j; t) = D_{OZ}(i, j; t) + \sum_{k=1}^{N} \sum_{t'=0}^{t} D_{OZ}(i, k; t - t')C(k, j; t'). \quad \text{Eqn. 4}$$

The direct correlation function can then be extracted from Eqn. 4 by Fourier transforming into frequency space, solving for $\hat{D}_{OZ}(i,j;f)$, and inverse-transforming back into the time domain. The branching ratio can subsequently be estimated using:

$$\sigma_{OZ} = \frac{1}{N} \sum_{i=1}^{N} \sum_{j \neq i}^{N} \sum_{t=0}^{T} D_{OZ}(i, j; t); \quad \text{Eqn. 5}$$

where T is a time beyond which one does not expect any direct correlations. For example, in practice, it is generally found that at times beyond 2-3 s, Eqn. 5 is not sensitive to choice of T. Once the branching ratio is determined, its mean value and fluctuations over time may be determined as well.

A more general method for determining branching ratio is based on a model similar to the node-based model 102. This model includes a set of nodes labeled by i=1 to N, each of which has an activation level A(i, t) that gives the total probability that node i fires at some point in the time interval (t−δt, t], where δt is the time step. Each node represents the local field average over some number of neurons near one microelectrode. Each nodal firing event corresponds to a population spike representing the near-simultaneous action potential discharge of a subpopulation of nearby neurons. The term nodal firing events is used to distinguish communal action potential discharges from other events, such as lower amplitude postsynaptic potentials. The activation level A(i, t) is determined by two factors. First, the probability that node i can fire spontaneously at time t, represented by the spontaneous firing probability S(i, t). Second, the probability that node i fires at time t due to firing at node j at some prior time, given by G(i, j;t). Since A(i, t) is the probability that node i fires, it can be mathematically expressed as one minus the probability that node i does not fire:

$$a(i, t + \delta t) = 1 - [1 - S(i; t)] \prod_{j=1}^{N} [1 - G(i, j; t)].$$ Eqn. 6

Non-Markovian connectivity can be introduced by allowing G(i, j;t) to depend on nodal firing events from node j which occurred at times preceding time t. This "memory" effect is most easily expressed by introducing a "memory kernel" H(i, j;t'). If H(i, j;t') is relatively large, then firing events at node j at a time t−t' will have a relatively large effect on the probability that node i will fire at time t. Conversely, if H(i, j;t') is small, then firing events at node j at an earlier time (t−t') will have a relatively small effect on the probability that node i will fire at time t. The mathematical expression of this relationship is given by:

$$G(i, j; t) = \sum_{t'=0}^{\infty} F(j; t - t') H_t(i, j; t');$$ Eqn. 7 where F(j;t)=1 if node j fires at time t and F(j;t)=0 otherwise. To build in non-Markovian long term potentiation or depression, one has to increase or decrease H(i, j;t') according to whether nodes i and j fire in the correct sequence with a given time interval t'. For example, for LTP, one may introduce a Hebbian learning factor $C_H(t')$ that gives the factor by which to increase H(i, j;t') if node j should fire at a time interval t' preceding firing at node i. The Hebbian learning rules, generalized for non-Markovian plasticity for LTP and LDP are respectively given by:

$$H_{t+\delta t}(i,j;t')=H_t(i,j;t')[1+C_H(t')F(i;t)F(j;t-t')]$$ Eqn. 8; and $$H_{t+\delta t}(i,j;t')=H_t(i,j;t')[1-C_H(t')(1-F(i;t))F(j;t-t')]$$ Eqn. 9.

The learning rule for spike timing dependent plasticity (STDP) is a combination of Eqn. 8 and Eqn. 9. In STDP learning, if node j consistently fires before node i, not only is the connection j→i strengthened, but the connection i→j is weakened. Connectivity may then be measured in terms of the branching and input ratios defined in Eqns. 2 and 3, where:

$$P(i, j; t) = \sum_{t'=0}^{\infty} H_t(i, j; t').$$ Eqn. 10

This model may be employed to extract the branching ratio from neural activity data and is useful because it is a learning model that can imitate the behavior of a real neural system. For example, if there are N experimental electrodes gathering neural activity data from a subject, then the simulated model can include N nodes and have a spontaneous firing probability S(n;t)=0 and a Hebbian learning factor $C_H(t)$=0.1 for all times from t=0 to t=1000 ms. The firing times of the simulated system F(n;t) can then be assigned the firing times for each electrode and STDP learning rules in accordance with Eqns. 8 and 9 may be applied. This causes the model to train on the experimental data, which will cause the memory kernels $H_t(i, j;t)$ to evolve in time according to the acquired neural activity data. If two nodes have a certain probability of firing in sequence with a certain probability, then the magnitude of that probability and the duration of the time delay will be reflected in the memory kernel between the two nodes. After the memory kernels reaches steady state values, the branching ratio may be extracted using equation Eqn. 2.

DESCRIPTION OF THE PREFERRED EMBODIMENT

Figure 4:
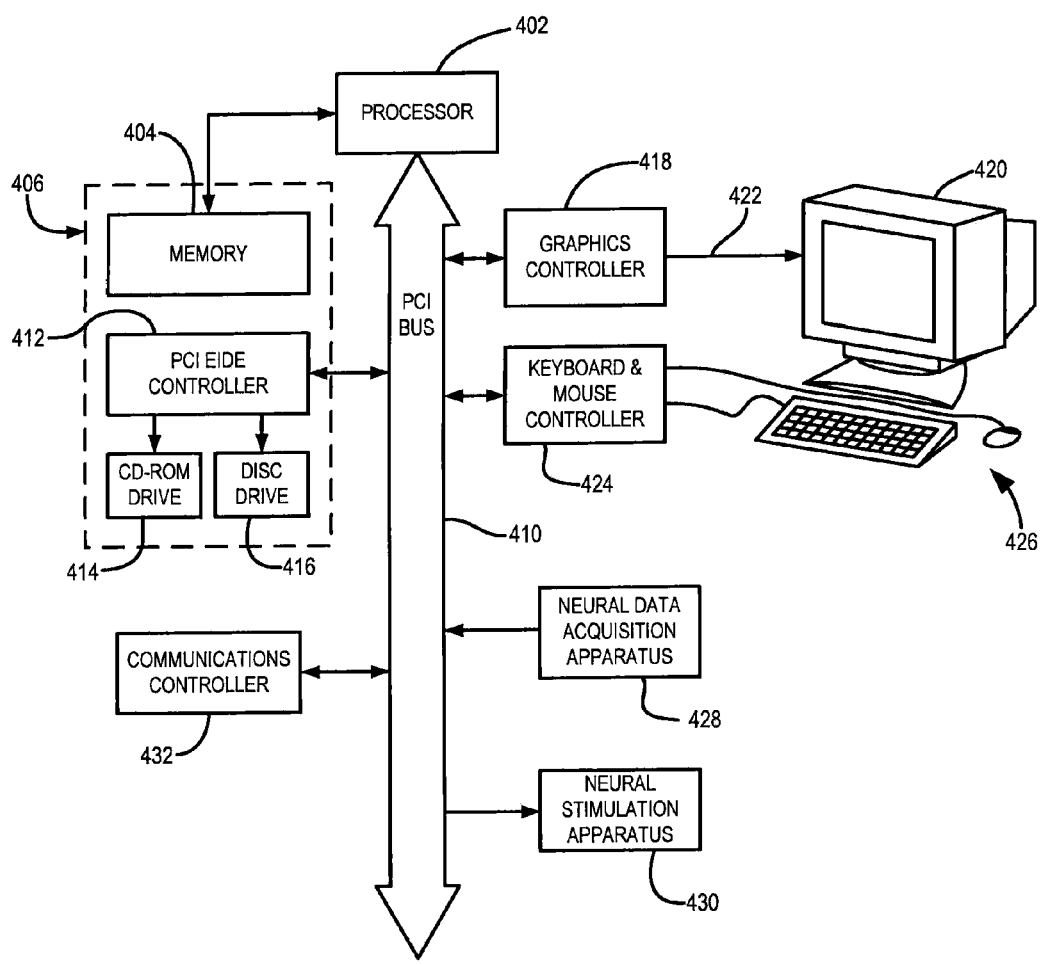
FIG. 4 is a schematic depiction of a system for suppressing and reversing epileptogenesis in accordance with the present invention.

Referring to FIG. 4, the present invention may be performed using a computer workstation including a processor 402 that executes program instructions stored in a memory 404 that forms part of the storage system 406. The processor 402 includes internal memory and I/O control to facilitate system integration and integral memory management circuitry for handling all external memory 404. The processor 402 also includes a bus driver that provides a direct interface with a multi-bus 410, which is an industry standard bus that transfers data between the processor 402 and a number of peripheral controller cards. These include a disc controller 412, which provides a high-speed transfer of data to and from a CD-ROM drive 414, and a disc drive 416. A graphics controller 418 couples the bus 410 to a monitor 420 through a standard VGA connection 422 and a keyboard and mouse controller 424 receives data that is manually input through a keyboard and mouse 426.

The bus 410 also connects to a neural data acquisition apparatus 428, such as an electroencephalograph (EEG) or magnetoencephalograph (MEG), that acquires neural activity data from a subject. A neural stimulation apparatus 430, such as an adapted deep brain stimulation (DBS) device, also connects to the bus 410 to allow electrical stimulation patterns determined by the workstation to be applied to a patient. Because electrical stimulation may be required on an ongoing basis, it is contemplated that the electrical stimulation device includes a power source, internal memory, and data processing capabilities so that it may be disconnected from the workstation. The bus 410 also connects to a communications controller 432 that connects to an intranet that links the workstation to one or more patient-data acquisition systems, a department PAC system, or institution data management system.

Figure 5:
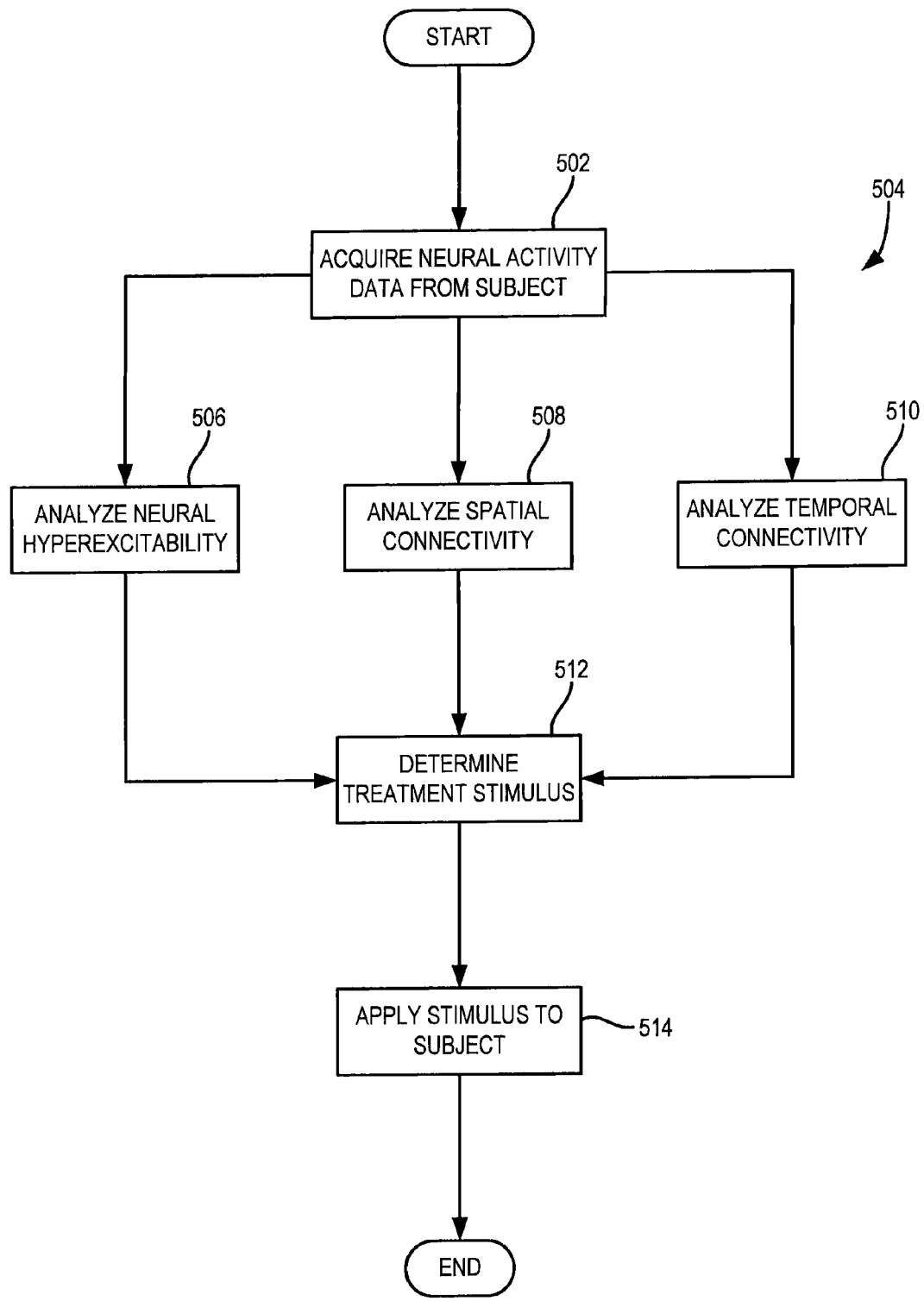
FIG. 5 is a flowchart setting forth a method for characterizing and treating epilepsy in accordance with the present invention.

Referring to FIG. 5, having outlined general definitions of and means of characterizing the three conditions for epilepsy, a method for reversing epilepsy that addresses each of these conditions and may be performed using the above-described workstation begins at process block 502 with the acquisition of neural activity data from the subject, for example, using the neural data acquisition apparatus 428. As indicated generally at 504, the acquired neural activity data is then analyzed to determine the degree to which the three conditions for epilepsy are present in the subject. A parameter indicative of neuronal hyperexcitability is generated at process block 506 using, for example, prior art techniques, such as monitoring the neuronal firing rate and averaging this over time.

At process block 508, connectivity in space is analyzed by determining the branching ratio σ from the acquired brain activity data. This may be performed using the above-discussed general method employing Eqns. 8 and 9 or the Ornstein-Zernike equation-based method, which employs Eqn. 4. Values of σ that are greater than one indicate overconnectivity in space. At process block 510, connectivity in time is characterized and a parameter indicative of temporal over-persistence is generated. For example, this may be achieved by identifying temporally recurrent signals in the acquired neural activity data and looking for micro-oscillations.

At process 512, the cumulative effect of the three conditions is analyzed to characterize eliptogenic patterns in the subject and determine a treatment that would reduce the risk of epilepsy. For example, intervention targeting neuronal hyperexcitability may also take into account interictal baseline activity and network connectivity, as simulations using the above-discussed model predict that suppression of neuronal firing rates to levels below a set point can result in compensatory supercritical connectivity (that is, spatial overconnectivity), which actually further promote epileptogenesis and result in the generation of seizure circuits. Likewise, spatial overconnectivity may be addressed by artificially and rapidly boosting spontaneous neural activity to near steady state values whenever the brain enters a supercritical state to relieve the drive towards supercritical connectivity. This counterintuitive idea arises directly from analysis of the computer model and it is contemplated that this may be one possible mechanism by which electrical brain stimulation works in the treatment of refractory epilepsy.

Temporal overconnectivity can be addressed by identifying learned seizure circuits, for example, A→B→C→A→B→C→etc, and "writing" onto the brain specific spatiotemporal patterns that cause the epileptic circuit to be rewritten or erased. For example, if a given seizure circuit is given by A→B→C, then electrical stimulation may be employed to activate the sequence B→A at random intervals. Similarly, another technique may include repeatedly activating the sequence A→B→C→X, where X is a random pattern that is different for each presentation. After repeated presentations of a random pattern X, it is expected that the recurrent loop A→B→C→A→B→C→etc can be broken and "unlearned".

After the treatment pattern is determined, then treatment is administered to the subject at process block 514 using, for example, stimulation apparatus 430 to apply selected electrical stimuli to the specified brain locations.

The present invention has been described in terms of the preferred embodiment, and it should be appreciated that many equivalents, alternatives, variations, and modifications, aside from those expressly stated, are possible and within the scope of the invention. Therefore, the invention should not be limited to a particular described embodiment

The invention claimed is:

1. A method for identifying and reducing a subject's risk of epilepsy, the method comprising:
   a) acquiring neural activity data from the subject;
   b) analyzing the acquired neural activity data by:
      b) i) calculating, from the acquired neural activity data, a parameter indicative of neuronal hyperexcitability due to imbalances between excitatory and inhibitory influences;
      b) ii) calculating, from the acquired neural activity data, a parameter indicative of spatial overconnectivity that leads to abnormally wide spreads of neuronal activity; and
      b) iii) calculating, from the acquired neural activity data, a parameter indicative of temporal overconnectivity that leads to abnormally persistent neuronal activity, wherein the parameter indicative of temporal overconnectivity accounts for non-Markovian effects;
   c) determining epileptic patterns in the subject based on the parameters calculated in step b); and
   d) administering a treatment to the subject configured to reverse the epileptic patterns determined in step c).

2. The method as recited in claim 1 wherein the neural activity data is acquired from the subject using at least one of electroencephalography and magnetoencephalography.

3. The method as recited in claim 1 wherein the parameter indicative of spatial overconnectivity calculated in step b)ii) is a branching ratio.

4. The method as recited in claim 3 wherein step b)ii) includes estimating the branching ratio using an adapted Ornstein-Zernike equation that is adapted to estimate a direct correlation function from a measured total correlation function.

5. The method as recited in claim 3 wherein step b)ii) includes estimating the branching ratio using a node-firing model including a memory kernel.

6. The method as recited in claim 1 wherein step d) includes applying a selected electrical stimulus to the brain to disrupt epileptogenic neural circuits.

7. The method as recited in claim 6 wherein the electrical stimulus is configured to disrupt the epileptogenic neural circuits by inducing a designated neural activity pattern at random intervals.

8. The method as recited in claim 6 wherein the electrical stimulus is configured to disrupt the epileptogenic neural circuits by inducing a random neural activity pattern at designated intervals.

9. The method as recited in claim 6 wherein the electrical stimulus is applied using a deep-brain-stimulation device.

10. The method as recited in claim 4 wherein step b)ii) includes:
    producing a cross-correlogram from the neural activity data acquired in step a), the produced cross-correlogram being indicative of a total correlation function; and
    estimating the direct correlation function using the produced cross-correlogram and the adapted Ornstein-Zernike equation.

11. The method as recited in claim 10 wherein step b)ii) includes estimating the branching ratio from the estimated direct correlation function.

* * * * *